United States Patent
Hanes

(10) Patent No.: US 8,084,674 B2
(45) Date of Patent: Dec. 27, 2011

(54) **FLOWER PIGMENTATION IN *PELARGONIUM HORTORUM***

(75) Inventor: Mitchell E. Hanes, Morgan Hill, CA (US)

(73) Assignee: Syngenta Participations AG, Basel (CH)

( * ) Notice: Subject to any disclaimer, the term of this patent is extended or adjusted under 35 U.S.C. 154(b) by 262 days.

(21) Appl. No.: 12/270,716

(22) Filed: Nov. 13, 2008

(65) Prior Publication Data

US 2009/0133151 A1    May 21, 2009

Related U.S. Application Data

(60) Provisional application No. 60/988,364, filed on Nov. 15, 2007.

(51) Int. Cl.
*A01H 1/00* (2006.01)
*A01H 4/00* (2006.01)
*A01H 5/00* (2006.01)
*A01H 5/10* (2006.01)

(52) U.S. Cl. ......... 800/323; 435/410; 800/260; 800/295
(58) Field of Classification Search ................... Plt./324, Plt./330, 332
See application file for complete search history.

(56) References Cited

U.S. PATENT DOCUMENTS

PP15,653 P2 *   3/2005   Hanes

OTHER PUBLICATIONS

Rud et al 2009 HortScience 44(4): 1020.*

* cited by examiner

*Primary Examiner* — David H Kruse
(74) *Attorney, Agent, or Firm* — S. Matthew Edwards

(57) ABSTRACT

The present invention relates to novel *Pelargonium hortorum*—interspecific plants having dark red to burgundy or darker pigmented flower petal, a trailing growth habit, dark leaf color and tolerance to high temperatures, high light and edema. The present invention also relates to methods for creating novel *Pelargonium hortorum*—interspecific hybrid plants having dark red to burgundy or darker pigmented flower petals, a trailing growth habit and tolerance to high temperatures, high light and edema.

10 Claims, 4 Drawing Sheets

FLOWER PIGMENTATION IN *PELARGONIUM HORTORUM*

CROSS-REFERENCE TO RELATED APPLICATIONS

This application is a nonprovisional and claims priority under 35 U.S.C. §119 to U.S. Provisional Application Ser. No. 60/988,364, filed Nov. 15, 2007, which is incorporated herein in their entirety by reference.

BACKGROUND OF THE INVENTION

The present invention relates to novel zonal geranium plants, *Pelargonium hortorum*—interspecific, having a trailing habit and dark-red to burgundy pigmented flower petals, a growth habit similar to an ivy geranium, green leaf color, tolerance to high light and temperature and non-sensitivity to edema. The present invention also relates to methods for creating novel *Pelargonium hortorum*—interspecific plants having pigmented flower petals. The present invention relates to a new and distinctive method of combining *Pelargonium* plants to produce new, distinct interspecific *Pelargonium* varieties. All publications cited in this application are herein incorporated by reference.

*Pelargonium hortorum* belongs to the family *Geraniaceae*. The exact origin of *Pelargonium hortorum* is unknown, but probably resulted from inter-crossing between several species native to South Africa including *P. zonale*, *P. inquinans*, *P. scandens* and *P. frutetorum*. Geraniums rank as one of the highest number of plants in terms of units sold among potted flowering plants and in terms of wholesale value. The traditional zonal geranium product has red, salmon, violet, white or pink flowers, green foliage, and is grown in 4-inch, 6-inch or gallon pots—the 4-inch product remains the bulk of the market.

There are basically 5 different types of *Pelargonium* in the market today. Zonal geraniums are the standard version of geraniums that are propagated vegetatively, by cuttings. Typically, they are tetraploid and have large 4-inch to 6-inch round flower heads with each flower having double blooms held well away from the plant foliage. The leaves are also large and sometimes up to 4-inches across. The plant habit tends to be rather upright and well branched generally growing to about 18-inches in one growing season. They are called zonal geraniums because many of them have zones or patterns in the center of the leaves. Varieties with self-branching habit and compact growth make tidy, well-shaped plants with a show of color all summer long. Some of the varieties have unusually dark green foliage which makes a particularly striking contrast to the colorful flower heads held above the foliage.

Seed geraniums are diploid plants grown from seed. They produce a more compact version of the zonal geranium, but with smaller single blooms on smaller 3-inch to 4" heads of blooms. These plants form low, compact mounds typically under a foot tall and wide. Seed geraniums are most often used in large landscape plantings and in smaller containers such as window boxes.

Named for both their habit and their ivy-like leaves, ivy geraniums typically have leaves that are stiff and shiny. The branches are long and trailing. Flower clusters on ivy geraniums are about 2-inches to 3-inches across. Plants can spread over 2-inches in one season. Ivy geraniums are great in hanging baskets and in window boxes and other containers.

Regal geraniums are great for early season color, but it is important to know they do not like the heat of summer and so they reduce the number of blooms they provide until the cool weather of fall.

Valued for their unique fragrances, scented geraniums are also worth growing for their distinctive foliage. While some varieties do occasionally bloom, scented geraniums usually are not grown for their flowers. The plant habit varies widely from one variety to another, as do leaf size, shape, color and texture.

Years ago, growers retained selected plants from the seasonal crops as stock plants for the subsequent season. These plants were maintained either in the greenhouse or planted outside for the summer and fall, then repotted and brought inside before the first frost. Cuttings were taken in winter, rooted, and maintained under minimum conditions until early spring for forcing. Several events precipitated a drastic change in this procedure. The economics of greenhouse space utilization combined with the development of "fast cropping" made the old procedures impractical. The development of serious systematic diseases almost always lead to the demise of the crop, mainly *Xanthomonas campestris* pv. *pelargonii* (bacterial wilt).

Today, vegetative material almost exclusively comes from specialized propagators that use culture-virus-indexing and other laboratory procedures to eliminate bacterial wilt and other systematic organisms such as vascular wilt, bacteria, virus, and fungi.

With any successful breeding program, there are numerous steps in the development of novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. For the horticultural industry, these important traits can include novel colors, resistance to diseases and insects, tolerance to drought and heat, or superior garden performance.

Traditionally, new traits are introduced into a breeder's germplasm through the combination of two individual plants that each possesses desirable characteristics. The parental lines are crossed and the progeny are evaluated for the presence of the desirable traits. Evaluation involves observing the progeny under different environmental conditions and at multiple times for the purpose of identifying any new expected and unexpected variations that may be useful. The new hybrid lines may be reproduced sexually or asexually. In the ornamental flowering plant industry, often times a particular characteristic, or set of characteristics, is not stable through several generations of sexual reproduction. The breeder may use asexual reproduction to propagate the variety, thus avoiding sexual recombination of traits and keeping the line uniform and stable.

The parents in a hybridization do not have to belong to the same species. Sometimes different species of the same genus will combine sexually in an interspecific cross. In some cases, different species readily combine in an interspecific cross to produce a hybrid plant. In other cases, barriers to combinability exist between species.

In order to introduce valuable economic traits such as disease resistance, flower shape and color, and heat or cold tolerance, from non-commercial species into the cultivar assortment, it is essential to overcome interspecific crossing barriers. Various techniques have been attempted to deal with some of these barriers, including in vitro isolated ovule pollination, in vitro embryo rescue, and ovary-slice and ovule culture. However, these techniques do not overcome the problem of chromosome mismatching and loss of chromosomes during meiosis and mitosis, barriers commonly encountered in interspecific crosses.

Sexual reproduction between individuals with different chromosome numbers, often the case in interspecific crosses, can be problematic. During sexual reproduction, each gametic chromosome must pair with its partner from the other parent's gamete. In this manner, the offspring receive a full complement of chromosomes, half of which originate from each parent. If the chromosome number of the parents is different, chromosome pairing does not occur correctly. Results of mismatched chromosome pairing may include the interspecific cross not producing offspring, the offspring produced being sterile, or the offspring produced being barely fertile.

One method for dealing with poor interspecific hybrid fertility is to look for naturally occurring 2n-gametes produced by the interspecific hybrid. Some plants frequently produce 2n-gametes, but others rarely do. Finding these 2n-gametes can be very difficult and time-consuming. Another method for restoring interspecific hybrid fertility is to double the chromosome number of the hybrid to produce an amphidiploid. This can be done using the chemical colchicine, which inhibits microtubule formation during cell division. When treated with colchicine, a cell's chromosomes are copied in preparation for mitosis as normal, but the lack of microtubules prevents cell cleavage. The result is an undivided cell that contains double the normal complement of the organism's chromosomes. The colchicine-treated cell is then regenerated into a full plant in which each cell has its chromosomes doubled. If an individual with mismatched chromosomes is treated with colchicine, its chromosomes will be doubled, thus creating a matching partner chromosome that is able to match up properly during sexual reproduction. The procedure can restore fertility to a formerly sterile individual and the newly fertile, amphidiploid plant can then produce segregating offspring that can be observed for further traits. Colchicine may also be used to double the chromosome number of a normal, cultivated plant so that the plant may be able to readily combine with another plant that has a different number of chromosomes. There is a range of ploidy levels among *Pelargonium* type. For example, cutting geraniums are typically tetraploid while seed geraniums are diploid.

Additionally, choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits can be used as parents to produce new populations for further selection.

These processes, which lead to the final step of marketing and distribution, require several from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several $F_1$. Selection of the best individuals can begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Therefore, there is a need for a method that combines *Pelargonium* species so that new important traits can be introduced into novel *Pelargonium* hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

This invention relates to novel *Pelargonium hortorum*—interspecific plants having dark red to burgundy or darker pigmented flower petals.

This invention further relates *Pelargonium hortorum*—interspecific plants having a trailing growth habit similar to ivy geraniums.

This invention also relates to plant parts of *Pelargonium hortorum*—interspecific of the present invention and tissue cultures thereof.

This invention further relates to *Pelargonium hortorum*—interspecific hybrids having dark red to burgundy or darker pigmented flower petals.

In addition, the present invention also relates to methods for creating novel *Pelargonium hortorum* plant having dark red to burgundy or darker pigmented flower petals using the *Pelargonium hortorum*—interspecific of the present invention as either a female or male parent in breeding.

The present invention also relates to an $F_1$ hybrid or a later generation *Pelargonium hortorum*—interspecific plant grown from the *Pelargonium hortorum*—interspecific seed produced by the aforementioned methods.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. An allele is any of one or more alternative forms of a gene, all of which relate to one trait or characteristic. In a diploid cell or organism, the two alleles of a given gene occupy corresponding loci on a pair of homologous chromosomes.

Aglycon (Alglycone). Aglycon is the non-sugar compound remaining after replacement of the glycosyl group from a glycoside by a hydrogen atom.

Anthocyanidin. Anthocyanidin is an extended conjugation made up of the aglycon of the glycoside anthocyanins.

Anthocyanin. Anthocyanins are a class of flavonoids based on the cyanidin structure, differing in the presence or absence of hydroxyl groups by methylation or glycosylation, forming colored pigments. They are glycosylated versions of cyanidin, pelargonidin or delphinidin. The conjugated bonds result in blue, red, and purple colors in flowers of plants; for example, Anthocyanin (Glycoside)=Anthocyanidin (Aglycon)+Sugar (Glycone).

Backcrossing. Backcrossing is a process in which a breeder repeatedly crosses hybrid progeny back to one of the parents, for example, a first generation hybrid $F_1$ with one of the parental genotypes of the $F_1$ hybrid.

Burning. A common trait in geraniums where the flower color turns dark on the edge.

Cyanidin. Cyanidin is the aglycon of cyaninin. In plants cyanidin is bound to a sugar molecule to form cyanidin-3-glucoside.

Diploid. A diploid is a cell or organism having a pair of each type of chromosome (homologous pair), so that the basic chromosome number is doubled.

Edema. A physiological disease of plants that is caused by watering practices. For example, a dry plant when watered, may suddenly absorb too much water causing cells on the leaves to burst which then causes corky, distorted areas on the leaves.

Essentially all the physiological and morphological characteristics. A plant having essentially all the physiological and morphological characteristics means a plant having the physiological and morphological characteristics of the recurrent parent, except for the characteristics derived from the converted trait.

Glycosylated. Glycosylated is the result of the addition of saccharides to proteins and lipids.

Growth habit. A general description as to how a plant grows. For example, a plant could have a trailing habit or an upright habit, or a plant could be compact in growth, vigorous or leggy.

Haploid. A haploid is a cell or organism having a single set of un-paired chromosomes.

Homozygous. Homozygous is a cell or organism having one or more gene loci on homologous chromosomes.

Hybrid. Hybrid means any offspring of a cross between two genetically unlike individuals (Rieger R., A. Michaelis and M. M. Green, 1968, A Glossary of Genetics and Cytogenetics, Springer-Verlag, N.Y.).

Inbred. An inbred means a substantially homozygous individual plant.

Inbreeding. In plants, inbreeding is a process in which a breeder crosses closely related plants increasing a plant's homozygosity.

Increased tolerance to edema. "Increased tolerance to edema" means plant varieties which show no edema or greatly reduced edema under stress conditions that would induce edema on more edema sensitive plant varieties.

Increased tolerance to light. "Increased tolerance to light" means plant varieties that can tolerate and thrive under summer, full-sun exposure in Gilroy, Calif. under field conditions, where peak light levels are measured at 1119 W per square meter. Ivy geraniums, for example, are stressed under these high light conditions and do well when grown under shade cloth that blocks 65% of this light.

Increased tolerance to heat. "Increased tolerance to heat" means plant varieties that can tolerate, Without adverse effects such as bleaching of the leaves, summer field temperatures reached in Gilroy, Calif. when placed in full-sun conditions, where peak temperatures measured at 104° F. with about a 40° F.-50° F. drop in temperature at nighttime.

Introgressive hybridization. The incorporation of genes of one species into the gene pool of another species. If the ranges of two species overlap and fertile hybrids are produced, they tend to backcross with the more abundant species. This process results in a population of individuals most of whom resemble the more abundant parents but which possess also some characters of the other parent species.

Ivy geranium. "Ivy geranium" means plants generally known as the species *Pelargonium peltatum*.

Malvidin. "Malvidin" is an anthocyanidin and as a primary plant pigment, its glycosides are highly abundant in nature. Malvidin is primarily responsible for example, for the color of red wine for the blue pigment found in the *Primula polyanthus* plant.

Open pollinated. A plant pollinated without human agency.

Pelargonidin. Pelargonidin is the aglycon of pelargoninin. In plants pelargonidin is bound to a sugar molecule to form pelargonidin-3-glucoside.

*Pelargonium*. A genus of plants in the family of *Geraniaceae*.

Peonidin. "Peonidin" is an anthocyanidin and a primary plant pigment which gives purplish-red hues to flowers.

Petunidin. "Petunidin" is an anthocyanidin or a monomeric anthocyanin.

Plant part or part of a plant. A plant part or part of a plant can include, but is not limited to cuttings, cells, protoplasts, cell tissue cultures, callus (calli), cell clumps, embryos, stamens, pollen, anthers, pistils, ovules, flowers, seed, petals, leaves, stems, and roots.

Ploidy. Ploidy means the number of single sets of chromosomes in a cell or an organism.

Quantitative Trait Loci (QTL). "Quantitative trait loci (QTL)" refer to genetic loci that control to some degree numerically representable traits that are usually continuously distributed.

Regeneration. "Regeneration" refers to the development of a plant from tissue culture.

Single gene converted (conversion). "Single gene converted" (or conversion) plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Tetraploid. A tetraploid is a cell or organism having a chromosome number that is four times the haploid number of chromosomes.

Tissue culture. A plant tissue culture indicates a composition comprising isolated cells of the same or a different type or a collection of such cells organized into parts of a plant.

Trailing growth habit. A trailing growth habit refers to plants where the plant width is greater than or equal to 2 times the plant height or the ratio of height/width is less than or equal to 0.5.

Zonal geranium. "Zonal geranium" means a tetraploid plant that has the general leaf type, plant habit, and appearance of *Pelargonium hortorum*.

DETAILED DESCRIPTION OF THE INVENTION

Figure 1:
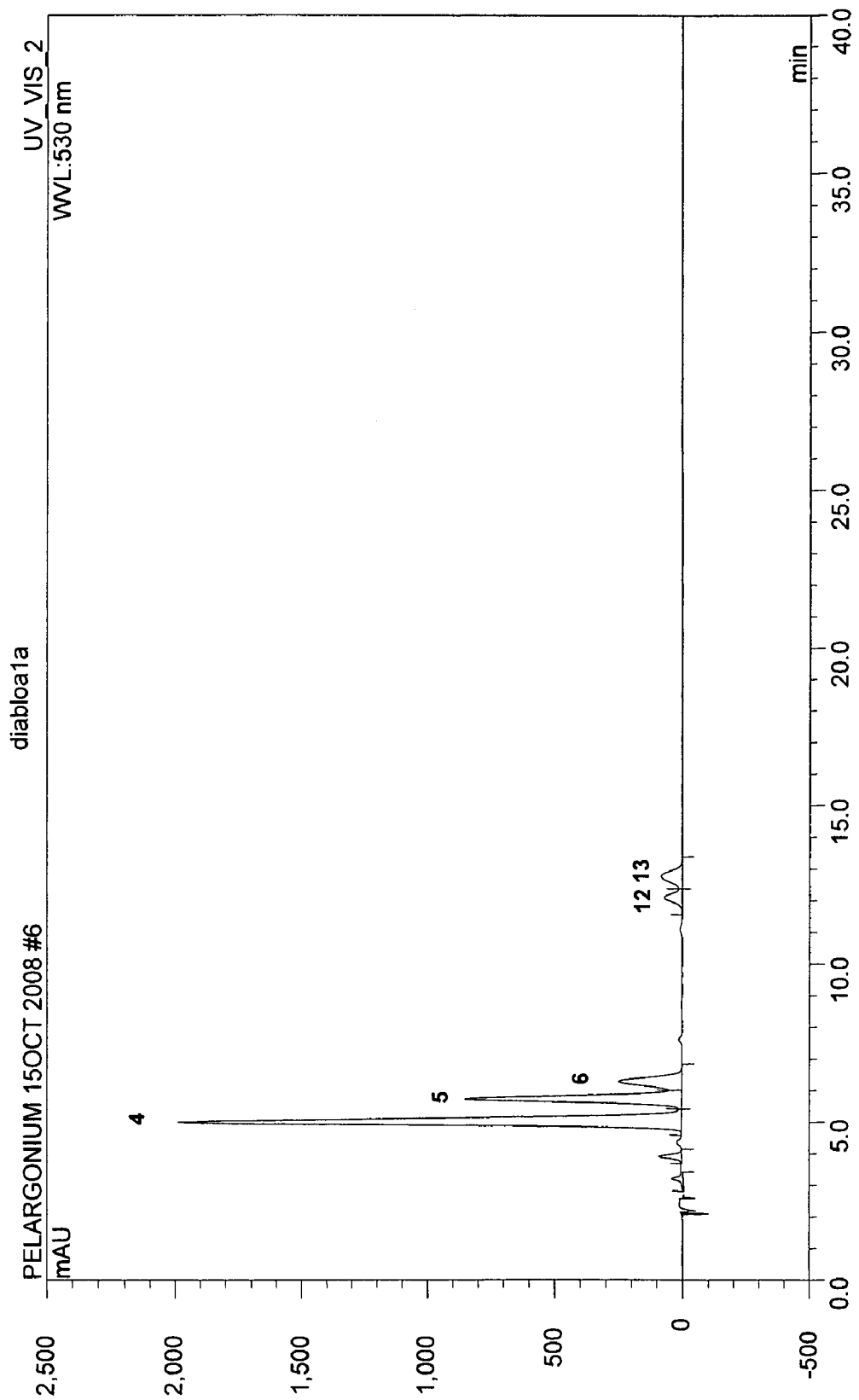
FIG. 1 provides a chromatogram showing the anthocyanin profile of the zonal comparison pelargonium 'Diablo'.
Figure 2:
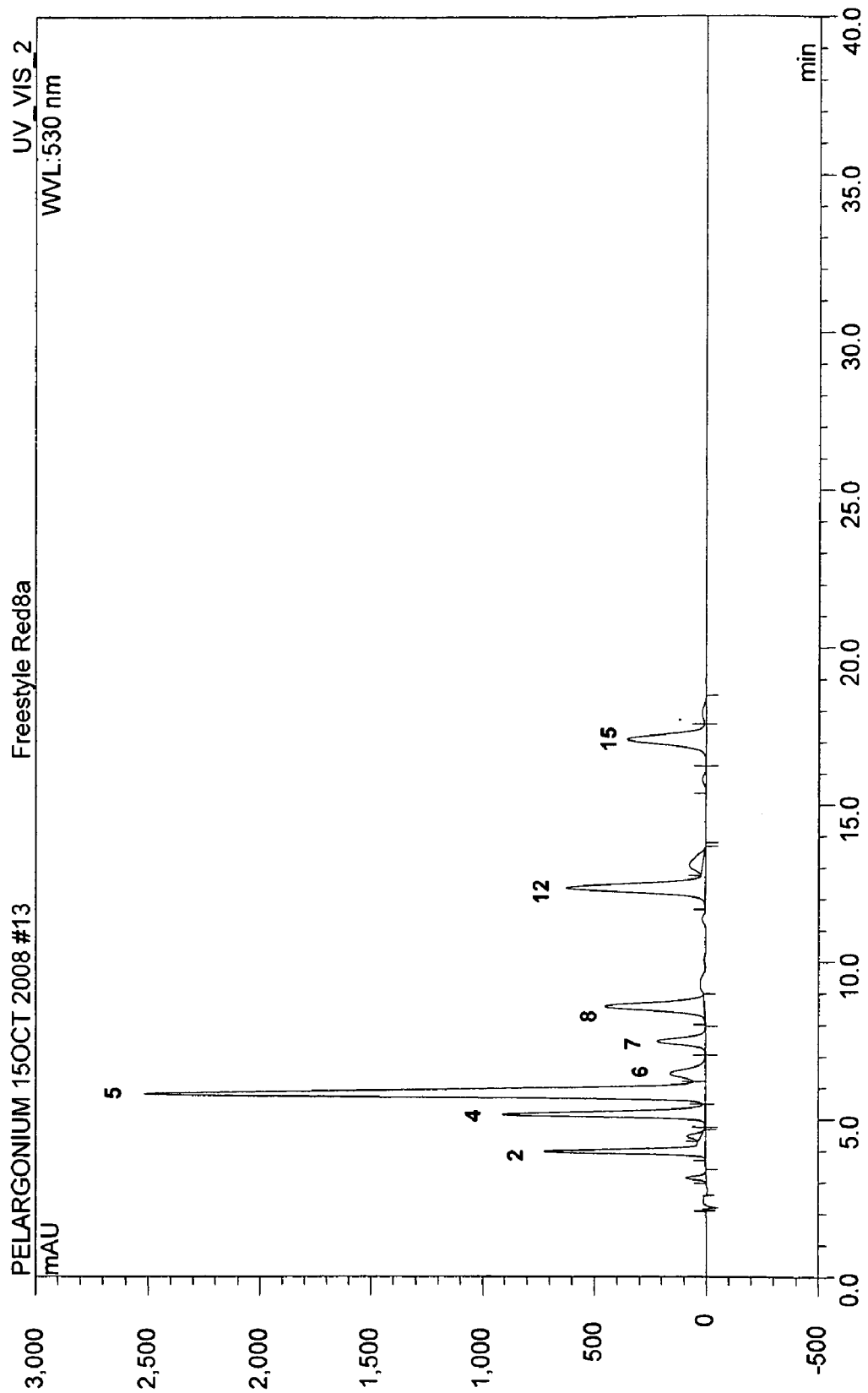
FIG. 2 provides a chromatogram showing the anthocyanin profile of an ivy pelargonium.
Figure 3:
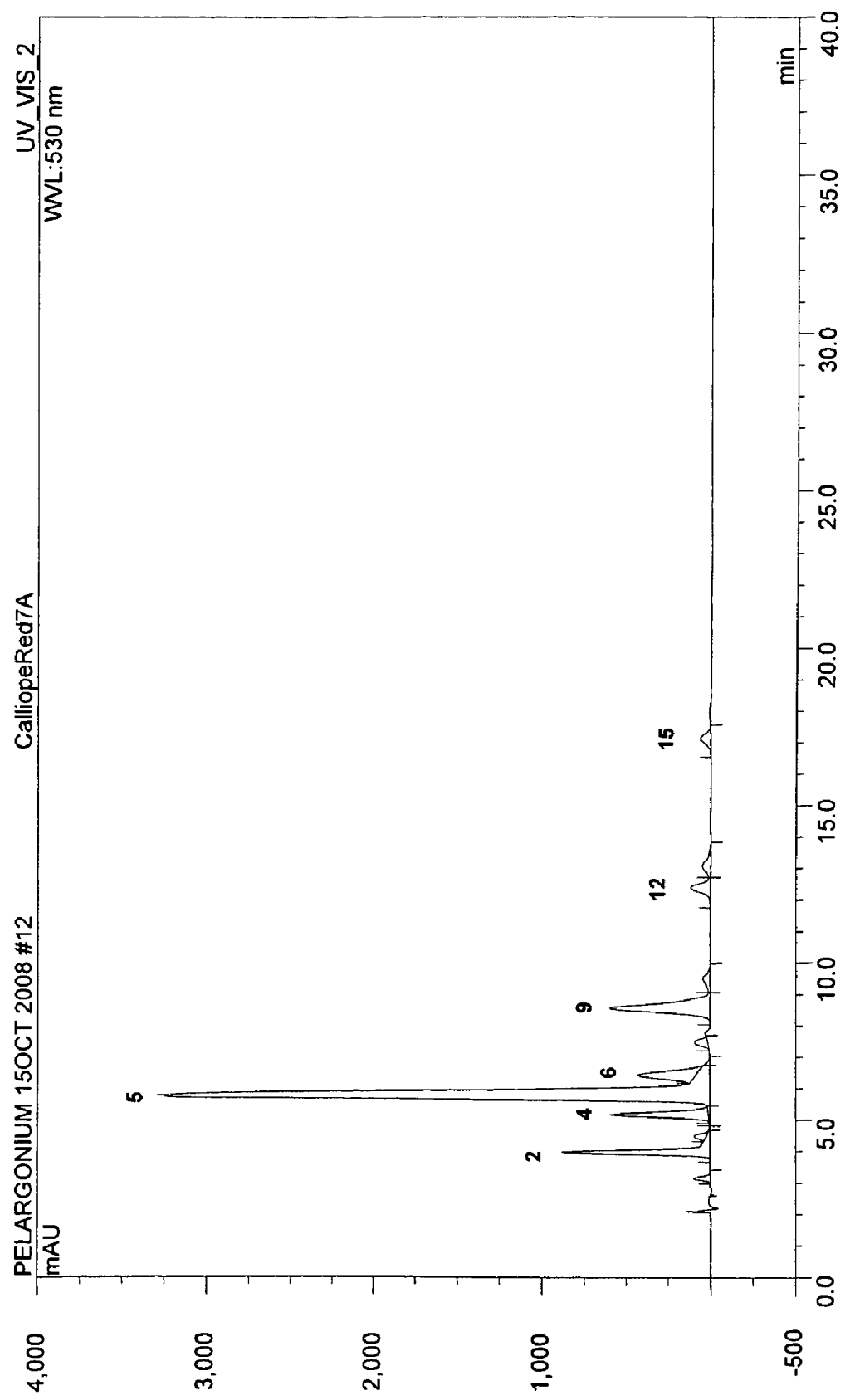
FIG. 3 provides a chromatogram showing the anthocyanin profile of the zonal interspecific pelargonium of the present invention, 'Calliope Dark Red'.

The present invention provides for *Pelargonium hortorum*—interspecific plants having dark red to burgundy or darker pigmented flower petals. The anthocyanins impart a range of dark red to burgundy to the *Pelargonium hortorum*—interspecific flower petals.

The present invention also provides for introgression of traits from plants of an ivy geranium into plants of a zonal geranium. The traits of the present invention can be introgressed into any *Pelargonium* species. The traits of the plants of the present invention are readily transferred between *Pelargonium* plants containing the desired traits into *Pelargonium* plants lacking the desired traits. The plants of the present invention can be used to modify the flower color of *Pelargonium* plants for commercial production. The crosses can be performed using either parent of the present invention as the pollen parent.

A plant of the present invention can be obtained by crossing a plant of the present invention with any *Pelargonium* lacking the desired traits of the present invention. The desired trait(s) may then be transmitted by sexual crossing to other *Pelargonium* plants if desired.

Additionally, the present invention provides for parts of the *Pelargonium hortorum*—interspecific plants having dark red to burgundy or darker pigmented flower petals. A plant part or part of a plant can include, but is not limited to cuttings, cells, protoplasts, cell tissue cultures, callus (calli), cell clumps, embryos, stamens, pollen, anthers, pistils, ovules, flowers, seed, petals, leaves, stems, and roots. More specifically the present invention relates to pollen, ovules, and cuttings of the *Pelargonium hortorum*—interspecific plants having dark red to burgundy or darker pigmented flower petals.

The present invention also provides for a tissue culture comprising regenerable cells of the *Pelargonium hortorum*—interspecific plants of the present invention. The tissue culture will preferably be capable of regenerating plants having the physiological and morphological characteristics of the described *Pelargonium hortorum*—interspecific plants, and of regenerating plants having substantially the same genotype as the described *Pelargonium hortorum*—interspecific plants. Preferably, the regenerable cells in such tissue cultures can be leaf, pollen, embryo, cotyledon, hypocotyl, meristematic cell, root, root tip, pistil, anther, flower, stem, ovule, petiole and the like. In addition, the present invention provides *Pelargonium hortorum* plants regenerated from the tissue cultures of the invention. Means for preparing and maintaining plant tissue culture are well known in the art. *Pelargonium hortorum* is a member of the *Geraniaceae* family and well-known to be amenable to tissue culture techniques. See for example, Madden, Jarren, I, et al., "Modes of regeneration in *Pelargonium×hortorum* (*Geraniaceae*) and three closely related species" In Vitro *Cellular and Developmental Biology*. (2005) 41(1):37-46.

The present invention further provides for pigments in the petals of *Pelargonium hortorum*—interspecific plants, where the pigment is composed of at least one anthocyanin and can be the glycosylated derivatives of cyanidin, or pelargonidin, or a combination thereof.

The present invention further provides for *Pelargonium hortorum* plants of the present invention having a plant width of at least about 18.5, 19.0, 19.3, 19.7, 20.2, 20.5, 20.8, 21.1, 21.6, 21.9, 22.3, 22.4, 22.7, 23.0, 23.5, 23.9, 24.1, 24.6, 24.9, 25.3, 25.4, 25.7, 26.2, 26.5, 27.0, 27.6, 28.2, 28.6, 28.7, 29.2, 29.7 and 30.0 inches.

The present invention further provides for *Pelargonium hortorum* plants of the present invention having a plant height of at least about 9.0, 9.2, 9.8, 10.1, 10.5, 10.8, 11.2, 11.6, 11.9, 12.3, 12.4, 12.8, 13.0, 13.5, 13.6, 13.9 and 14.0 inches or higher and including all integers and fractions thereof.

The present invention further provides for *Pelargonium hortorum* plants of the present invention having a total anthocyanin content of at least about 25.35, 26.0, 26.8, 27.3, 28.7, 29.3, 31.3, 31.2, 31.6, 32.5, 33.7, 34.6, 35.4, 36.6, 37.8, 40.1, 42.3, 43.8, 44.9, 45.7, 46.8, 47.2, 48.9, 51.6 percent, or higher and including all integers and fractions thereof. The present invention also encompasses a total anthocyanin content ranging for example, between 25% to 32.5%, between 28.7% to 43.8% or between 29.3% to 47.20%, including all integers and fractions thereof.

In addition, the present invention further provides for a method of producing a first generation ($F_1$) hybrid *Pelargonium hortorum*—interspecific plant with dark red to burgundy or darker pigmented flower petals. The method involves crossing a first parent *Pelargonium hortorum*—interspecific plant with a second parent *Pelargonium hortorum*—interspecific plant and harvesting the resultant first generation ($F_1$) hybrid *Pelargonium hortorum*—interspecific seed, and selecting a hybrid plant. Either or both of the first parent or second parent *Pelargonium hortorum*—interspecific plants can be a *Pelargonium hortorum*—interspecific plant of the present invention. Additionally, the present invention relates to a first generation ($F_1$) hybrid *Pelargonium hortorum*—interspecific plant or a part thereof produced by the method described above.

The present invention further provides for methods for developing *Pelargonium* plants in a plant breeding program using plant breeding techniques including parental selection and hybrid development, recurrent selection, backcrossing, pedigree breeding, restriction fragment length polymorphism enhanced selection, genetic marker enhanced selection and transformation. Seeds, *Pelargonium* plants, and parts thereof produced by such breeding methods are also part of the invention.

The invention further provides for methods for developing *Pelargonium* hybrid plants in a plant breeding program using plant breeding techniques including parental selection and hybrid development, recurrent selection, backcrossing, pedigree breeding, restriction fragment length polymorphism enhanced selection, genetic marker enhanced selection and transformation. Embryos, *Pelargonium* hybrid plants, and parts thereof produced by such breeding methods are also part of the invention.

The present invention also provides for viable *Pelargonium hortorum*—interspecific and *Pelargonium* hybrid seeds and plants and succeeding generations thereof which are grown from seeds of the present invention.

Flower color is predominantly due to two types of pigment: flavonoids and carotenoids. Flavonoids contribute to a range of colors from yellow to red to blue. Carotenoids impart a reddish-orange or yellow tinge and are commonly the only pigment in yellow or orange flowers. The flavonoid molecules which make the major contribution to flower color are the anthocyanins which are glycosylated derivatives of cyanidin, delphinidin, petunidin, peonidin, malvidin and pelargonidin, and are localised in the vacuole. The different anthocyanins can produce marked differences in color. Flower color is also influenced by co-pigmentation with colorless flavonoids, metal complexation, glycosylation, acylation, methylation and vacuolar pH. See for example, Forkman, G., *Plant Breeding* (1991) 106:1-26.

The present invention also provides for *Pelargonium* plants that not sensitive to edema. Edema is a physiological disorder that affects geraniums, causing the leaves to yellow and die. Ivy geraniums are particularly sensitive to this disorder. Edema is thought to be caused by an imbalance of the plant's water uptake and water loss. Water retention in the cells is thought to cause some cells to burst, so as the broken tissue heals, it becomes dry and corky. Ed. John W. White. Geraniums IV. Chapter 25 "Foliar Diseases" Ball Publishers pp. (1993) 221-222.

The following examples are set forth as representations of specific and preferred embodiments of the present invention. These examples are not to be construed as limiting the scope of the invention in any manner. It should be understood that many variations and modifications can be made while remaining within the spirit and scope of the invention.

EXAMPLES

The trailing zonal geranium types of the present invention can be described as a dark red and burgundy geranium color of at least but darker than RHS 46B. The present invention's unique combination of color(s), growth habit, high temperature tolerance, and full sun tolerance does not exist in the present flower industry. The closest color that is currently available for geraniums in the zonal class can best be described as a deep scarlet, where occasionally plants will have RHS 46B used to describe only a darker vein or a petal edge which fades to a lighter red. Because these red-colored geraniums are approximately 50% of the market, the plants of the present invention will encompass new dark red-colored geraniums, which will have the potential for significant utility. Also the unique growth habit of the plants of the present invention will have utility for use in both hanging baskets and as landscape items.

Example 1

Development of the Plants of the Present Invention by Introgressing Traits from *P. peltatum* to *P. hortorum*

The dark red to burgundy or darker petal colors of the plants of the present invention are the result of many generations of crossing and selecting plants of *Pelargonium hortorum* crossed with *Pelargonium* peltatum. The breeding process involved 14 generations of crosses and selections, using at least 10 different ivy geraniums in the process. The unique colors in the zonal interspecific plants of the present invention are derived from ivy geraniums (*Pelargonium peltatum*). Because ivy geraniums usually cannot be successfully grown in full-sun and are sensitive to the physiological disease known as edema, the new zonal interspecific plants of the present invention are a new and novel development.

The process of breeding and selecting the zonal interspecific plants of the present invention has resulted in plants that have the utility of both a zonal geranium and an ivy geranium. The plants of the present invention have been selected to maximize the positive traits and to eliminate the weakness in each of these *Pelargonium* species. The flower petal color and the growth habit are positive traits derived from the ivy geranium. The darker leaf color, tolerance to high light, tolerance to high temperature and a non-sensitivity to edema are positive traits derived from the zonal geranium.

The dark red to burgundy or darker colors of the flower petals of the present invention are also non-burning. Burning is a common trait with darker scarlet red colors in the full-sun where the flower petal color tends to turn dark on the edge, giving the petals an unattractive, burnt look.

The plants of the present invention are trailing, zonal plants, which can be grown in 4-inch, 6-inch, or 8-inch pots or can be used in 10-inch baskets.

Example 2

Differences in Plant and Height Width Between Plants of the Present Invention and Americana Dark Red Table 1 compares the differences in plant width and plant height between 2 selections of the present invention and the commercial zonal geranium variety, 'Americana Dark Red'. '10426-1' is a trailing dark red selection of the present invention and '10612-1' is a dark red trailing selection of the present invention. The plant widths and heights were taken in a cultivated field in Gilroy Calif. on Oct. 18, 2007. Columns one and two show the plant width and height in inches of selection '10426-1' of the present invention, columns three and four show the plant width and plant height in inches of selection '10612-1' of the present invention and columns 5 and 6 show the plant width and height of zonal geranium 'Americana Dark Red'. Rows 18 and 19 show the averages and the standard deviation. Note that the selections of the present inventions have an unexpectedly greater plant width than 'Americana Dark Red'.

TABLE 1

Comparison of plant height and width between two selections of the present invention and 'Americana Dark Red'.

| 10426-1 | | 10612-1 | | Americana Dark Red | |
|---|---|---|---|---|---|
| Width | Height | Width | Height | Width | Height |
| 29 | 10 | 25.5 | 9 | 28 | 14 |
| 25 | 12 | 25 | 11 | 18 | 12 |
| 28 | 10 | 23 | 9.5 | 21 | 14 |
| 26 | 12 | 25 | 9.5 | 20 | 12.5 |
| 25 | 10 | 21 | 9 | 17 | 10 |
| 28 | 9 | 20 | 9 | 21 | 12 |
| 26 | 10 | 24 | 13 | 20 | 13 |
| 24 | 11 | | | 23 | 16 |
| 24 | 10 | | | 20 | 12 |
| 24 | 9.5 | | | 19.5 | 11.5 |
| 24.5 | 10.5 | | | 17 | 10 |
| 29 | 10 | | | 16 | 11 |
| | | | | 16 | 12.5 |
| | | | | 15.5 | 10 |
| | | | | 18.5 | 10.5 |
| Average 26.0 | 10.3 | 23.4 | 10.0 | 19.4 | 12.1 |
| Std. Dev. 2.0 | 0.9 | 2.1 | 1.5 | 3.2 | 1.7 |

Example 3

Anthocyanin Analysis of *Pelargonium* Petals

Flower petals can be analyzed for their anthocyanin content. Methods for anthocyanin analysis are well-known in the art. Please See Zhang, Z., et al., *J. Agric. Food Chem.* (2004) 52:688-691 and Kazuma, K., et al., *Phytochemistry* (2004) 62: 229-237. Sample methods of analysis include a comparison of HPLC profiles of the hydrolysates with anthocyanidin standards, with spectrophotometric quantification of anthocyanins as their aglycons.

Flower tissue from 10 different *Pelargonium* cultivars was analyzed to determine the flavonoid and anthocyanin content in the dried petal tissue. The ten *Pelargonium* cultivars tested were: 'Diablo' (zonal geranium), 'Tango Dark Red' (zonal geranium), 'Rocky Mountain Dark Red' (zonal geranium), 'Tango 09' (zonal geranium), 'Designer Dark Red' (zonal geranium), 'Samba' (zonal geranium), 'Calliope Dark Red' (zonal-looking geranium with zonal interspecific background), 'Freestyle Dark Red' (ivy geranium), 'Americana Dark Red' (zonal geranium) and 'Eclipse Velvet Red' (zonal-looking geranium with zonal interspecific back ground).

Freeze dried tissue was used for the analysis of flavonoid content in the different cultivars. Three samples of approximately 25 mg of ground freeze-dried petal tissue from each cultivar was extracted at room temperature overnight with 10 ml of a methanol:acetic acid:water (70:3:27) solution. The samples were centrifuged for 4 minutes at 10,000 rpm The supernatant was removed and the pellet was re-extracted in 10 ml of a methanol:acetic acid:water (90:1:9) solution. The resulting samples were centrifuged for 4 minutes at 10,000 rpm. The supernatant was removed and combined with the first supernatant to give the crude extract. The extract was dried in-vacuo in a SAVANT SC210 SPEEDVAC to near dryness and made up to a final volume of 1 ml in an 80% methanol (methanol:acetic acid:water (80:2:18) solution. The extracts were centrifuged and the flavonoids analysed by high performance liquid chromatography (HPLC), using a DIONEX 3000 ULTIMATE solvent delivery system with a PHENOMENEX LUNA (5 μm, 150×4.6 mm) RP-18 column (column temperature 25° C.) and a DIONEX 3000 PDA detector. Elution (0.8 ml min$^{-1}$) was performed using a solvent system comprising solvent A [HOAc:$CH_3$CN:$H_3PO_4$:$H_2O$ (20:24:1.5:54.5)] and 1.5% $H_3PO_4$ (solvent B) and a linear gradient starting with 35% A, increasing to 67% A at 20 minutes, 90% A at 23 minutes and 100% A at 29.3 minutes, remaining at 100% A for a further 10 minutes. Flavonoids were detected at 350 nm and anthocyanins were detected at 530 nm. Flavonoid levels were determined as quercetin-3-O-rhamnoglucoside (Apin Chemicals, Abingdon, Oxon, UK) equivalents, and the anthocyanins as cyanidin 3-O-glucoside (Extrasynthese, Genay, France) equivalents.

Total flavonoid and anthocyanin content from the petal extracts was also calculated from absorbance readings at 350 and 530 nm respectively, using extinction coefficients ($E^{1\%}_{1cm}$) of 14300 and 35000. Absorbance readings were made on a JASCO V-530 UV/V is spectrophotometer (Jasco, Tokyo, Japan). Results are reported as the mean of the three replicates.

Anthocyanidins were obtained by adding 6 ml of 3N HCL to 100 mg DW (dry weight) of petal tissue in tall glass test tubes. The tubes were then left for 45 minutes at 95° C. The extract was transferred to 15 ml plastic tubes and centrifuged at 3,000 rpm for 15 minutes. The supernatant was transferred to a new 15 ml tube and the pellet discarded. One ml of ethyl acetate was added and the tubes centrifuged again at 3,000 rpm for 3 minutes. The aqueous phase was removed to a new test tube and approximately 500 ul of amyl alcohol added to partition the anthocyanidins. The anthocyanidins were dried down under nitrogen, dissolved in 80% methanol and then run on the HPLC as above. Anthocyanidins were not quantified but the HPLC separation allowed the relative percentages of the different anthocyanidins to be determined for the extracts from the *pelargonium* cultivars.

The total anthocyanin concentrations in the flower petals for the different *pelargonium* cultivars are reported in Table 2. Column one shows the *pelargonium* cultivar and column 2 shows the total anthocyanin content in each cultivar expressed as mg of anthocyanin per gram of dry weight of petal and columns 3-8 show the total percentage of each anthocyanidin, pelargonidin, cyaniding, peonidin, delphinidin, malvidin and petunidin, respectively, found in the petals of each cultivar. 'Calliope Dark Red' and 'Eclipse Velvet Red' are selections produced by the plants of the present invention.

Results show that the total anthocyanin content of the zonal interspecific *pelargoniums* of the 'Calliope Dark Red' and 'Eclipse Velvet Red' were unexpectedly significantly higher than the comparison zonal geraniums and that the total anthocyanin content of 'Calliope Dark Red' and 'Eclipse Velvet Red' unexpectedly approached the total anthocyanin content of the comparison ivy geranium, 'Freestyle Dark Red'.

When the total anthocyanin content of 'Calliope Dark Red' is compared to the total anthocyanin content of the comparison zonal geraniums, 'Calliope Dark Red' has a total anthocyanin content that is approximately 1.5-2.0 times greater than the comparison zonal geranium cultivars. The pelargonidin content of 'Calliope Dark Red' was significantly reduced (about 13.9%) when compared to the comparison zonal geraniums (about 53.5%-77.0%). The cyanidin content of 'Calliope Dark Red' was significantly increased (about 20.7%) when compared to the comparison zonal geraniums (about 1.6%-10.1%) and the peonidin content was significantly increased (about 56.1%) when compared to the comparison zonal geraniums (about 15.4%-24.2%).

When the total anthocyanin content of 'Eclipse Velvet Red' is compared to the total anthocyanin content of the comparison zonal geraniums, 'Eclipse Velvet Red' has a total anthocyanin content that is approximately 1.2-1.7 times greater than the comparison zonal geranium cultivars. The pelargonidin content of 'Eclipse Velvet Red' was significantly reduced (about 18.6%) when compared to the comparison zonal geraniums (about 53.5%-77.0%). The cyanidin content of 'Eclipse Velvet Red' was significantly increased (about 10.5%) when compared to the comparison zonal geraniums (about 1.6%-10.1%) and the peonidin content was significantly increased (about 50.2%) when compared to the comparison zonal geraniums (about 15.4%-24.2%).

The data further shows that the zonal interspecific selections of the present invention, 'Calliope Dark Red' and 'Eclipse Velvet Red', have unexpectedly, a total anthocyanin content and anthocyanidin profile approaching ivy *pelargoniums* instead of zonal *pelargoniums*.

Pelargonidin was the predominant anthocyanidin in the zonal *pelargonium* lines, along with reasonable amounts of peonidin and malvidin. The Ivy *pelargonium* line, 'Freestyle Dark Red' and the two selections of the present invention, 'Calliope Dark Red' and 'Eclipse Velvet Red' have peonidin as the major anthocyanidin, with reasonable amounts of cyanidin and pelargonidin. Some fluctuation in malvidin is seen but with no obvious pattern. All six main anthocyanidins were detected across the range of *pelargonium* cultivars but not all were present in each individual *pelargonium* cultivar.

TABLE 2

Total anthocyanin concentration and relative percentage of the different anthocyanidins present in an anthocyanin extract from dried petal tissue of selected *Pelargonium* cultivars.

| Cultivar | Anthocyanin (mg · gDW) | Total percentage of each anthocyanidin | | | | | |
|---|---|---|---|---|---|---|---|
| | | Pelargonidin | Cyanidin | Peonidin | Delphinidin | Malvidin | Petunidin |
| 'Diablo' (zonal) | 18.12 | 72.7 | 1.6 | 15.4 | 0.3 | 10.0 | 0 |
| 'Tango Dark Red' (zonal) | 19.62 | 70.0 | 5.0 | 16.4 | 1.2 | 6.6 | 0.9 |
| 'Rocky Mountain Dark Red' (zonal) | 24.01 | 68.2 | 2.4 | 19.6 | 0.7 | 8.6 | 0.5 |
| 'Tango 09' (zonal) | 21.64 | 77.0 | 1.6 | 18.5 | 0 | 2.9 | 0 |
| 'Designer Dark Red' (zonal) | 23.61 | 53.5 | 2.2 | 24.2 | 0.7 | 18.7 | 0.8 |
| 'Samba' (zonal) | 25.30 | 67.2 | 2.6 | 21.7 | 0.7 | 7.3 | 0.5 |
| 'Calliope Dark Red' (zonal interspecific) | 36.70 | 13.9 | 20.7 | 56.1 | 3.4 | 4.3 | 1.0 |
| 'Freestyle Dark Red' (ivy) | 38.02 | 25.7 | 16.0 | 51.9 | 2.1 | 3.3 | 1.1 |
| 'Americana Dark Red' (zonal) | 23.90 | 57.6 | 10.1 | 19.1 | 1.9 | 9.9 | 1.3 |
| 'Eclipse Velvet Red' (zonal interspecific) | 31.06 | 18.6 | 10.5 | 50.2 | 6.5 | 12.6 | 1.8 |

Total anthocyanin concentration is the mean value from 3 extracts (samples).

Figure 4:
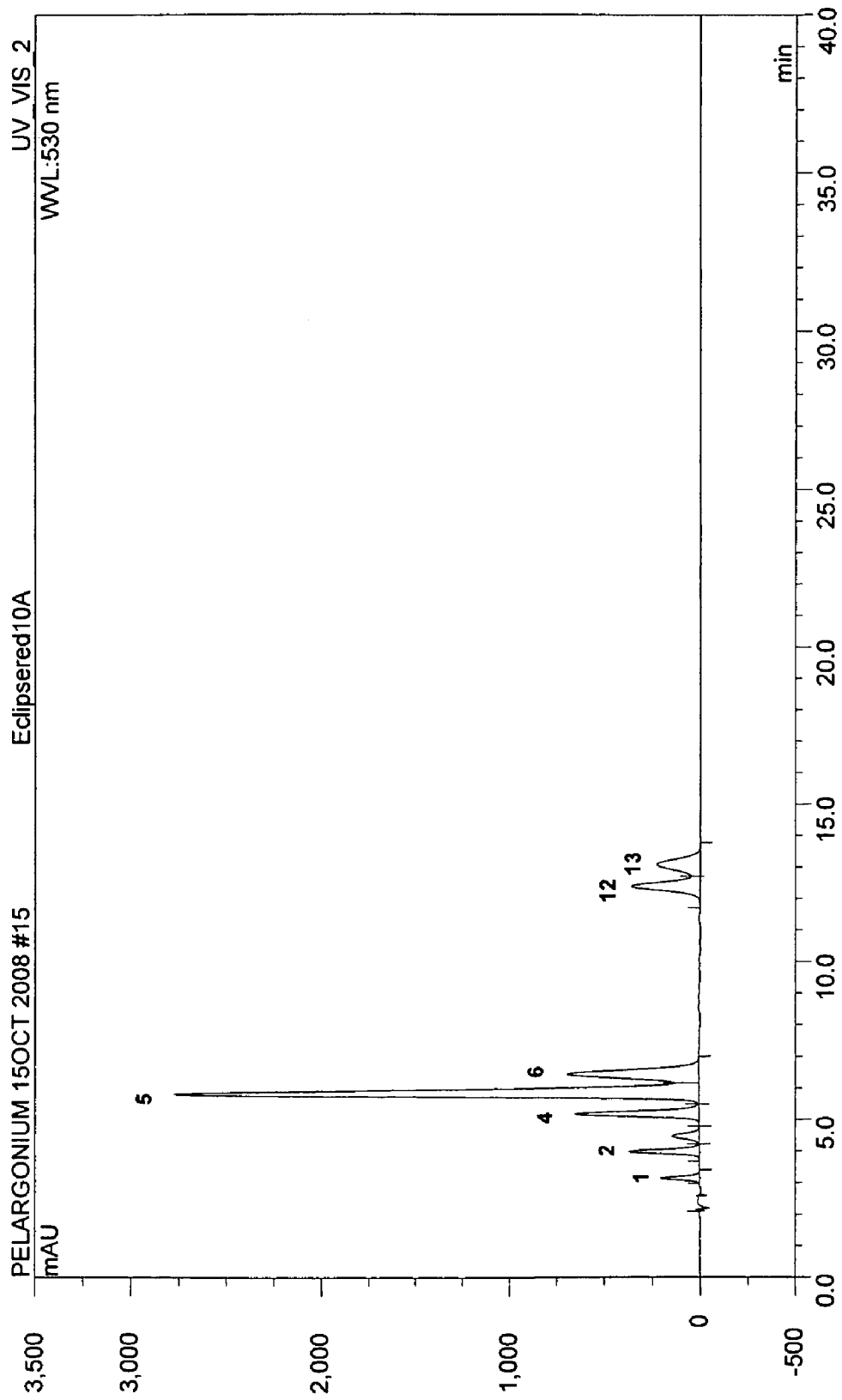
FIG. 4 provides a chromatogram showing the anthocyanin profile of the zonal interspecific pelargonium of the present invention, 'Eclipse Velvet Red'.

Individual anthocyanin profiles are presented in Table 3 and FIGS. 1-4. Actual anthocyanin identities have not been established. The likely base of anthocyanidin is surmised for each peak and based on the spectra maxima for each peak. The results are in agreement with previous work that reported the major anthocyanins in red flowered *Pelargonium* cultivars are the 3,5 diglucosides of Pelargonidin, Peonidin, delphinidin and malvidin or their acetylated derivatives. Mitchell, K. A., Markham, K. R., Boase, M. R. (1998). Pigment chemistry and colour of *Pelargonium* flowers. *Phytochemistry* 47(3): 355-361. The anthocyanin profiles as shown from chromatograms show the differences between the ivy *pelargonium* (FIG. 2) and the zonal comparison *pelargonium*, 'Diablo' (FIG. 1) and the zonal interspecific *pelargoniums* of the present invention, 'Calliope Dark Red' (FIG. 3) and 'Eclipse Velvet Red' (FIG. 4). The peaks are labeled as per Table 3.

The zonal interspecific selections of the present invention have resulted in a change in pigment content for zonal *pelargoniums*, which have a predominance of dihydroxylated anthocyanins (peonidin and cyanidin based) as in ivy *pelar-*

*goniums*, whereas the zonal *pelargoniums* have a predominance of the monohydroxylated anthocyanidin (pelargonidin), likely resulting in a more maroon or mauve-red colored flower as opposed to an orange-red flower.

TABLE 3

Anthocyanin peaks detected in extracts of different *Pelargonium* cultivars.

| | Anthocyanin Peaks from Chromatogram | | | | | |
|---|---|---|---|---|---|---|
| Cultivar | Pk 1 (min 3.1) Cy/Pe | Pk 2 (min 3.9) Pel | Pk 3 (min 4.4) CY/Pe | Pk 4 (min 5.1) Pel | Pk 5 (min 5.8) Cy/Pe | Pk 6 (min 5.8) Del/Mal/Pet |
| Diablo | 0.07 | 0.23 | 0 | 10.50 | 4.45 | 1.71 |
| Tango Dark Red | 0.22 | 1.00 | 0.12 | 9.96 | 4.10 | 1.60 |
| Rocky Mountain Dark Red | 0.15 | 0.45 | 0.15 | 11.10 | 6.13 | 2.93 |
| Tango 09 | | 0.31 | 0.09 | 11.46 | 6.38 | 1.42 |
| Designer Dark Red | 0.08 | 0.32 | 0.18 | 7.37 | 6.58 | 6.19 |
| Samba | 0.15 | 0.61 | 0.12 | 11.54 | 6.87 | 2.24 |
| Calliope Dark Red | 0.23 | 3.31 | 0.18 | 2.31 | 22.01 | 2.08 |
| Freestyle Dark red | 0.21 | 3.02 | 0.18 | 4.23 | 15.69 | 1.24 |
| Americana Dark Red | 0.35 | 1.91 | 0.43 | 8.75 | 6.35 | 3.96 |
| Eclipse Velvet Red | 0.53 | 1.31 | 0.58 | 2.95 | 15.89 | 5.18 |

| | Anthocyanin Peaks from Chromatogram | | | | | |
|---|---|---|---|---|---|---|
| Cultivar | Pk 7 (min 7.4) Pel | Pk 8 (min 7.7) | Pk 9 (min 8.5) Cy/Pe | Pk 10 (min 9.5) Cy/Pe | Pk 11 (min 11.3) Pel | Pk 12 (min 12.3) Cy/Pe |
| Diablo | | | | | | 0.44 |
| Tango Dark Red | | | | | 0.07 | 1.07 |
| Rocky Mountain Dark Red | | 0.48 | | | | 0.99 |
| Tango 09 | | 0.79 | | | | 0.63 |
| Designer Dark Red | | 0.20 | | | | 0.60 |
| Samba | | | | | 0.09 | 1.67 |
| Calliope Dark Red | 0.31 | | 4.21 | 0.33 | | 0.78 |
| Freestyle Dark red | 1.24 | | 3.14 | | 0.05 | 5.03 |
| Americana Dark Red | 0.62 | 0.60 | 0.06 | | | 0.37 |
| Eclipse Velvet Red | | | | | | 2.65 |

| | Anthocyanin Peaks from Chromatogram | | | | |
|---|---|---|---|---|---|
| Cultivar | Pk 13 (min 12.9) Del/Mal/Pet | Pk 14 (min 15.8) Pel | Pk 15 (min 17.1) Cy/Pe | Pk 16 (min 17.9) Del/Mal/Pet | Total Anthocyanin (mg · gDW) |
| Diablo | 0.72 | | | | 18.12 |
| Tango Dark Red | 1.47 | | | | 19.62 |
| Rocky Mountain Dark Red | 1.63 | | | | 24.01 |
| Tango 09 | 0.62 | | | | 21.64 |
| Designer Dark Red | 2.12 | | | | 23.61 |
| Samba | 2.03 | | | | 25.30 |
| Calliope Dark Red | 0.48 | | 0.47 | | 36.70 |
| Freestyle Dark red | 0.62 | 0.07 | 3.18 | 0.13 | 38.02 |
| Americana Dark Red | 0.95 | | | | 23.90 |
| Eclipse Velvet Red | 2.16 | | | | 31.06 |

Concentrations are reported as mg · g$^{-1}$ DW (in cyanidin 3-glucoside equivalents). Table reports concentration and the likely type of anthocyanin, not actual identity. Pel = pelargonidin, Cy = cyanidin, Pe = Peonidin, Del = delphinidin, Mal = malvidin, Pet = Petunidin.

Example 4

**Preparation of a Zonal *Pelargonium* Plant with Altered Flower Color/Pattern by Using the Plants of the Present Invention and by Performing Additional Breeding and Selection Methods**

Another method of the present invention is a *Pelargonium hortorum*—interspecific plant or *Pelargonium* hybrid having increased petal anthocyanin levels greater than about 1.2 times more than comparison zonal *pelargoniums* by performing additional breeding and selection until zonal *pelargonium* selections with increased pigmentation concentration are obtained. For example, a zonal *pelargonium* with an altered flower color pattern is produced by crossing an interspecific *pelargonium* plant of the present invention, harvesting the seed produced by the cross, and planting and growing the seed thereby producing an ornamental plant with an altered flower color and/or altered flower color pattern.

Example 5

**Increased Edema Tolerance of the Plants of the Present Invention when Compared to Comparison Ivy *Pelargonium* Cultivars**

A study was conducted in Gilroy, Calif. from January to April 2007 and 2008 under greenhouse conditions and from June to September 2007 and 2008 under outdoor field conditions to determine the difference in edema tolerance between the zonal interspecific plants of the present invention and ivy *pelargoniums*. Ivy *pelargoniums* have been observed to be susceptible to edema, while under the same growing conditions the zonal *pelargoniums* are completely free of edema. The physical manifestation of edema on a plant leaf can be best described as small, translucent fluid-filled blisters/pustules which forms mainly on the leaves but can occur on the stems and sometimes on the flowers. When plants of the zonal interspecific plants of the present invention were under pressure from severe edema, the leaves of the zonal interspecific plants of the present invention did not exhibit any physical symptoms of edema, while in comparison, the leaves of the ivy *pelargonium* plants exhibited extensive blistering and scarring. These results indicate that while the zonal interspecific *pelargonium* plants of the present invention take on the color and habit characteristics of ivy *pelargoniums*, they retain the tolerance to edema that is seen in zonal *pelargonium* plants.

Example 6

**Increased Heat/Temperature Tolerance of the Plants of the Present Invention when Compared to Other *Pelargonium* Varieties**

A temperature study was conducted in Gilroy, Calif. from Jun. 1, 2008 to Sep. 30, 2008 under outdoor field conditions to determine the difference in heat/temperature tolerance between the zonal interspecific plants of the present invention and other comparison *pelargoniums*. Outdoor temperatures were measured at 5 minute intervals using a digital outdoor thermometer. Temperatures ranged from approximately 45° F. to about 104° F. When comparing the physical effects of the high heat/temperature on the plants, it was observed that the zonal interspecific plants of the present invention tolerated the combination of higher temperatures and increased light levels than the comparison *pelargonium* plants.

Example 7

**Increased Light Tolerance of the Plants of the Present Invention when Compared to Ivy *Pelargoniums***

A light study was conducted in Gilroy, Calif. from Jun. 1, 2008 to Sep. 30, 2008 under outdoor field conditions to determine the difference in heat/temperature tolerance between the zonal interspecific plants of the present invention and other comparison *pelargoniums*. Outdoor light intensity was measured at 5 minute intervals using a light and temperature sensor made by Argus Control Systems LTD and recorded by version 11.11 firmware software. Light was measured in $Wm^2$ and ranged from 4 $\mu m^2$ to 1081 $Wm^2$. When comparing the physical effects of the high light on the plants, it was observed that the zonal interspecific plants of the present invention tolerated higher light than the comparison ivy *pelargonium* plants. When grown under high light and high temperatures the zonal interspecific plants of the present invention had green foliage and robust growth while the comparison ivy *pelargoniums* had cholorotic foliage and poorly growing plants.

Further Embodiments of the Invention

Additional Breeding Methods for *Pelargonium*

One method of recurrent selection entails individual plants cross pollinating with each other to form progeny. The progeny are grown and the superior progeny selected by any number of selection methods, which include individual plant, half-sib progeny, full-sib progeny, selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids.

Mass selection can be used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Backcross breeding can be used to move the progeny toward the genotype of the recurrent parent but at the same time retain many components of the non-recurrent parent by stopping the backcrossing at an early stage and proceeding with selfing and selection. For example, an $F_1$, such as a commercial hybrid, is created. This commercial hybrid may be backcrossed to one of its parent lines to create a $BC_1$ or $BC_2$. Progeny are selfed and selected so that the newly developed inbred has many of the attributes of the recurrent parent and yet several of the desired attributes of the non-recurrent parent.

Pedigree breeding starts with the crossing of two genotypes, such as a plant from the present invention and one other elite line having one or more desirable characteristics that is lacking or which complements the plants of the present invention. If the two original parents do not provide all the desired characteristics, other sources can be included in the breeding population. In the pedigree method, superior plants are selfed and selected in successive filial generations.

Pedigree is a method used by breeders of ordinary skill in the art to describe the varieties. Varieties that are more closely related by pedigree are likely to share common genotypes and combinations of phenotypic characteristics. All breeders of ordinary skill in the art maintain pedigree records of their breeding programs. These pedigree records contain a detailed description of the breeding process, including a listing of all parental lines used in the breeding process and information on how such line was used. A breeder of ordinary skill in the art would know if the plant of the present invention was used in the development of a progeny line, and would also know how many crosses to a line other than the plant of the present invention or to the plant of the present invention as a parent or other progenitor were made in the development of any progeny line.

Mutation breeding is one of many methods that could be used to introduce new traits into plants derived from the plants of the present invention. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of the plants of the present invention that comprises such mutation.

Traits are also used by those of ordinary skill in the art to characterize progeny. Traits are commonly evaluated at a significance level, such as a 1%, 5% or 10% significance level, when measured in plants grown in the same environmental conditions. For example, a mutant or backcross conversion of the plants of the present invention may be characterized as having the same morphological and physiological traits as the plants of the present invention.

Breeding with Molecular Markers

Molecular markers also provide a means by which those of ordinary skill in the art characterize the similarity or differences of two lines. Using the breeding methods described herein, one can develop individual plants, plant cells, and populations of plants that retain at least 25% and, up to 99.5% genetic contribution from the plants of the present invention, as measured by either percent identity or percent similarity. In pedigree analysis the percentage genetic contribution may not be actually known, but on average 50% of the starting germplasm would be expected to be passed to the progeny line after one cross to another line, 25% after another cross to a different line, and so on. With backcrossing, the expected contribution of the plants of the present invention after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing the plants of the present invention.

Isozyme Electrophoresis and RFLPs have been widely used to determine genetic composition. Isozyme Electrophoresis has a relatively low number of available as markers and a low number of allelic variants. RFLPs allow more discrimination because they have a higher degree of allelic variation. Both of these methods have been eclipsed by SSRs SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

All plants produced by the use of the methods described herein and that retain the unique genetic or trait combinations of the plants of the present invention are within the scope of the invention. Progeny of the breeding methods described herein may be characterized in any number of ways, such as by traits retained in the progeny, pedigree and/or molecular markers. Combinations of these methods of characterization may be used.

Tissue Culture

As it is well known in the art, tissue culture of *Pelargonium* can be used for the in vitro regeneration of *Pelargonium* plants. Tissues cultures of various tissues of *Pelargonium* and regeneration of plants therefrom are well known and published. By way of example, a tissue culture comprising organs has been used to produce regenerated plants as described in In Vitro Regeneration and *Agrobacterium* Transformation of *Echinacea purpurea* Leaf Explants, Korock, A. et al., 2002, in J. Janick and A. Whipkey (eds.), *Trends in new crops and new uses*, p 522-526; Regeneration and Micropropagation: Techniques, Systems and Media 1991-1995, in Herman, E. B., ed., *Recent Advances in Plant Tissue Culture*, Volume 3 (1995); Desamero et al., *Plant Cell Tiss. Org. Cult.* 33:265-271 (1993); Tabei et al., *Plant Tiss. Cult. Lett.* 10:235 (1993). Thus, another aspect of this invention is to provide cells which, upon growth and differentiation, produce *Pelargonium* plants having the physiological and morphological characteristics of the plants of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

With the advent of molecular biological techniques allowing the isolation and characterization of genes that encode specific protein products, scientists in the field of plant biology developed a strong interest in engineering the genome of plants to contain and express foreign genes, or additional or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention in particular embodiments also relates to transformed versions of the claimed plants of the plants of the present invention and progeny therefrom.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *Pelargonium* plants, using transformation methods as described below to incorporate transgenes into the genetic material of the *Pelargonium* plant(s).

Backcrossing

Persons of ordinary skill in the art will recognize that when the term *Pelargonium* plant is used in the context of the present invention, this also includes derivative varieties that retain the essential distinguishing characteristics of the plants of the present invention, such as a Single Gene Converted (Conversion) plant of the plants of the present invention or a transgenic derivative having one or more value-added genes incorporated therein (such as herbicide or pest resistance). Backcrossing methods can be used with the present invention to improve or introduce a characteristic into the variety. The term "backcrossing" as used herein refers to the repeated crossing 1, 2, 3, 4, 5, 6, 7, 8, 9 or more times of a hybrid progeny back to the recurrent parents. The parental *Pelargonium* plant which contributes the gene for the desired characteristic is termed the nonrecurrent or donor parent. This terminology refers to the fact that the nonrecurrent parent is used one time in the backcross protocol and therefore does not recur. The parental *Pelargonium* plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until an *Pelargonium* plant is obtained wherein essentially all of the desired morphological and physiological characteristics of the recurrent parent are recovered in the converted plant, in addition to the single gene transferred from the nonrecurrent parent, as determined at the 5% significance level when grown under the same environmental conditions.

DEPOSIT INFORMATION

A deposit of the Goldsmith Seeds, Inc. seed of the proprietary *Pelargonium hortorum*—interspecific 9876-3(M)OP disclosed above and recited in the appended claims have been made with National Collections of Industrial Food and Marine Bacteria (NCIMB), 23 St. Machar Drive, Aberdeen, Scotland, AB24 3RY, United Kingdom. The date of deposit was Nov. 12, 2007. The deposit of seed was taken from the same deposit maintained by Goldsmith Seeds, Inc. since prior to the filing date of this application. All restrictions upon the deposits have been removed, and the deposits are intended to meet all of the requirements of 37 C.F.R. §1.801-1.809. The NCIMB accession number for *Pelargonium hortorum*—interspecific 9876-3(M)OP is NCIMB 41515.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed:

1. A *pelargonium* seed designated 9876-3(M)OP wherein a representative sample of seed was deposited under NCIMB No. 41515.

2. A *pelargonium* plant, or a part thereof, produced by growing the seed of claim 1.

3. A tissue culture of cells produced from the plant of claim 2, wherein said cells of the tissue culture are produced from a plant part selected from the group consisting of seed, leaf, pollen, embryo, cotyledon, hypocotyl, meristematic cell, root, root tip, pistil, anther, flower, stem, and petiole.

4. A protoplast produced from the plant of claim 2.

5. A protoplast produced from the tissue culture of claim 3.

6. A *pelargonium* plant regenerated from said tissue culture of claim 3.

7. A method for producing hybrid *pelargonium* seed comprising crossing a first parent *pelargonium* plant with a second parent *pelargonium* plant and harvesting the resultant hybrid *pelargonium* seed, wherein said first parent *pelargonium* plant and/or second parent *pelargonium* plant is the *pelargonium* plant of claim 2.

8. A hybrid *pelargonium* plant produced by growing said hybrid *pelargonium* seed of claim 7.

9. Hybrid progeny of the *pelargonium* plant designated 9876-3(M)OP deposited under NCIMB No. 41515, wherein said progeny has at least one or more desired traits selected from the group consisting of increased tolerance to light, increased tolerance to heat and increased tolerance to edema.

10. A method of introducing one or more desired traits, wherein said trait is selected from the group consisting of increased tolerance to light, increased tolerance to heat and increased tolerance to edema into a *pelargonium* plant wherein the method comprises:
  (a) crossing the *pelargonium* plant designated 9876-3(M)OP deposited under NCIMB No. 41515 that comprises one or more desired traits selected from the group consisting of tolerance to high light, tolerance to high temperatures and tolerance to edema with a second parent *pelargonium* plant lacking said traits; and
  (b) selecting one or more progeny plants that have the one or more desired traits;
  (c) crossing the selected progeny plants with the 9876-3(M)OP plants to produce backcross progeny plants;
  (d) selecting for backcross progeny plants that have the desired trait and all of the physiological and morphological characteristics of 9876-3(M)0P; and
  (e) repeating steps (c) and (d) three or more times in succession to produce selected fourth or higher backcross progeny plants that comprise the desired trait and all of the physiological and morphological characteristics of 9876-3(M)OP.

* * * * *